US00PP08312P

United States Patent [19]

Vletter

[11] Patent Number: Plant 8,312

[45] Date of Patent: Jul. 20, 1993

[54] LILY PLANT NAMED D'OLERON

[75] Inventor: Floris Vletter, Rijnsburg, Netherlands

[73] Assignee: Gebr. Vletter & J. A. Den Haan, Rijnsburg, Netherlands

[21] Appl. No.: 796,692

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A distinct cultivar of lily plant named D'Oleron, characterized by its uniform light red-purple color, with yellow at the base, vigorous growth habit, horizontal flowers, and by its strongly reflexed flower tips.

1 Drawing Sheet

The present invention comprises a new and distinct cultivar of lily, botanically known as Lilium, known commercially as Lilium oriental hybrid, and hereinafter referred to by the cultivar name D'Oleron. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the primary objectives of creating new lily cultivars having a distinctive pink flower color; horizontal flowers and sufficiently long stems to permit use of D'Oleron as cut flowers.

The new cultivar was originated from a hybridization made by the inventor in a controlled breeding program in Rijnsburg, The Netherlands in 1981. The female parent was the cultivar Stargazer, and the male parent was an unnamed seedling.

The new cultivar was discovered and selected as one flowering plant within the progeny of the stated cross by the inventor in July 1981 in a controlled environment in Rijnsburg, The Netherlands.

The first act of asexual reproduction of the new cultivar was accomplished by the inventor when scales were taken from the initial selection in 1985 in a controlled environment in Rijnsburg, The Netherlands.

Horticultural examination of selected units has demonstrated that the combination of characteristics as herein disclosed for the new cultivar are firmly fixed and are retained through successive generations of asexual reproduction.

The new cultivar has not been observed under all possible environmental conditions. The phenotype may vary somewhat with variations in environment such as temperature, light intensity, and day length, without, however, varying the genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of D'Oleron which in combination distinguish this lily as a new and distinct cultivar.

1. Uniform red-purple flower color;
2. The base area of the petal is yellow, with the yellow color extending well along the midvein;
3. Flowers have a generally horizontal attitude;

4. The tips of the flowers are strongly reflexed at the tips;
5. Vigorous growth habit.

Of the many commercial cultivars known to the present inventor, the most similar in comparison to the new cultivar is Acapulco, disclosed in a pending application of the present inventor. In comparison to Acapulco, the new cultivar has horizontal flowers and the top surface tepal color is a significantly lighter red-purple. When flowering is forced under natural light, D'Oleron produces an inflorescence approximately 19 days earlier than Stargazer, under the same growing conditions. D'Oleron is fertile.

The accompanying photographic drawing shows typical flower characteristics of the new cultivar, with colors being as true as possible with illustrations of this type. The photograph comprises a top perspective view showing several flowers and buds at various stages.

In the following description, color references are made to The Royal Horticultural Society (RHS) Colour Chart. The color values were determined at Wageningen in 1988–1989 and at Rijnsburg in July 1991.

Origin: Seedling from Breeding Program.

Parentage:

*Seed parent.*—Stargazer.

*Pollen parent.*—Unnamed seedling.

Classification:

*Botanical.*—Lilium.

*Commercial.*—Oriental hybrid.

THE PLANT

Form: A single stem carrying numerous pedicels alternately arranged.

Height: Medium; 105 cm at time of opening of anthers of first flower.

Growth habit: Vigorous.

Stem: Color 145A; Circular in transverse section; internodal length uniform, 2 cm; anthocyanin pigmentation present.

Foliage:

*Quantity.*—40–50 leaves depending on growing conditions.

*Size of leaf.*—Mature leaves are short to medium in length, 14 cm; and medium in width, 4 cm.

*Shape of leaves.*—Elliptical.

*Texture.*—Smooth with weak glossiness; no pubescence.

*Color.*—Medium green 137A.

Bulbs:

*Size.*—Outlet 6–30 cm.

*Color.*—Purplish brown.

Roots: Both stem and contractile present.

THE BUD

Form: Tapering (like a lancet).

Size: 10 cm.

Opening: Unfolds normally.

Color: 63B prior to opening.

Tepals: Folded, three visible.

THE FLOWER

Blooming habit: Raceme.

Size: Approximately 17 cm in diameter, depending on growing conditions.

Borne: Horizontal.

Shape: Generally in form of hexagonal star; bowl-shaped in cross section.

Tepalage:

*Number of tepals.*—Six.

*Arrangement.*—Three inner and three outer; each with slight marginal undulation.

*Color.*—Upper surface: Light purple 73C. Lower surface: Light purple 73C-D.

*Spotting or marking.*—Dark pink spots, each of which have a diameter of 1 mm; yellow to green colored strip with white edges at base of each tepal.

Nectaries and papillae: Present.

Pedicel:

*Length.*—9 cm (the first flower).

*Color.*—Medium green with anthocyanin.

*Form.*—Curved.

Texture: Papillose.

Disease resistance: No disease problems noted to date.

Fragrance: Absent or very weak.

Lasting quality: Excellent.

REPRODUCTIVE ORGANS

Stamens, anthers:

*Arrangement.*—Anthers form a generally circular pattern.

*Length.*—Short, 7 cm.

*Number.*—Six.

*Filaments.*—Light green.

Pollen color: Light brown to orange brown.

Anther color: Brown with purple.

Pistils: Green style; total length of pistil 8 cm.

Stigma: Triangular grey.

Ovaries: Triangular in shape; other characteristics typical of oriental lily varieties.

I claim:

1. A new and distinct cultivar of lily plant named D'Oleron, as illustrated and described.

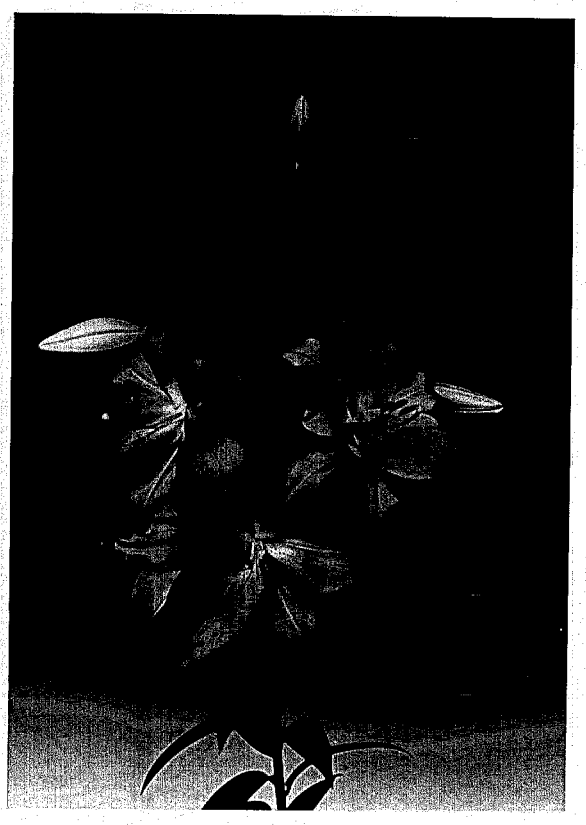

* * * * *